United States Patent [19]
Koiso et al.

[11] Patent Number: 6,127,290
[45] Date of Patent: *Oct. 3, 2000

[54] HEAT GENERATOR FOR FOOTWEAR AND MANUFACTURING METHOD THEREOF

[75] Inventors: Yasuhiko Koiso; Naoto Wagatsuma; Masako Yamakawa; Minako Suzuki, all of Hiratsuka, Japan

[73] Assignee: Japan Pionics Co., Ltd., Tokyo, Japan

[*] Notice: This patent is subject to a terminal disclaimer.

[21] Appl. No.: 08/965,146

[22] Filed: Nov. 6, 1997

[30] Foreign Application Priority Data

Nov. 6, 1996 [JP] Japan ................................. 8-310154
Nov. 25, 1996 [JP] Japan ................................. 8-329193

[51] Int. Cl.⁷ ................................. B32B 5/16; B32B 1/04
[52] U.S. Cl. ........................... 442/72; 428/327; 442/284; 442/286; 442/290; 442/389; 442/392; 442/393
[58] Field of Search ................................. 428/327; 442/72, 442/284, 286, 290, 389, 393, 392; 126/204

[56] References Cited

U.S. PATENT DOCUMENTS

| | | |
|---|---|---|
| 4,496,415 | 1/1985 | Sprengling . |
| 5,425,945 | 6/1995 | Koiso et al. ................................. 428/74 |
| 5,472,541 | 12/1995 | Simmons et al. . |

FOREIGN PATENT DOCUMENTS

| | | |
|---|---|---|
| 0271278 | 6/1988 | European Pat. Off. . |
| 0 370 600 | 5/1990 | European Pat. Off. . |
| 0 427 475 A1 | 5/1991 | European Pat. Off. . |
| 0 506 336 A1 | 9/1992 | European Pat. Off. . |
| 59-71618 | 5/1984 | Japan . |
| 62-011528 | 1/1987 | Japan . |
| 7-059809 | 3/1995 | Japan . |
| 8-112303 | 5/1996 | Japan . |
| 8-173471 | 7/1996 | Japan . |
| WO 96/11654 | 4/1996 | WIPO . |

*Primary Examiner*—Blaine Copenheaver
*Assistant Examiner*—John J. Guarriello
*Attorney, Agent, or Firm*—Nixon Peabody LLP; Thomas W. Cole

[57] ABSTRACT

Provided is a heat generating bag for footwear having a comfortable temperature regardless of the state of use, namely, when staying still, walking etc., which is thin and avoids an uncomfortable feeling of the wearer. The heat generating bag for footwear is made by having a heat generating composition powder and hot-melt adhesive powder held in the pores of multiporous vegetable fiber non-woven fabrics, such fabrics being heat compressed on a mold compressor, and the obtained sheet shaped heat generating body being packed in an air-permeable bag. The heat composition is held in the pores of multiporous vegetable fiber non-woven fabric layers which are superposed by the adhesion of water. Such non-woven fabric are compressed on a mold compressor, and the obtained sheet shaped heat generating body is impregnated with water or an inorganic electrolyte and then packed in an air-permeable bag.

6 Claims, 3 Drawing Sheets

HEAT GENERATOR FOR FOOTWEAR AND MANUFACTURING METHOD THEREOF

BACKGROUND OF THE INVENTION

1. Field of the Invention

The present invention relates to a heat generating bag for footwear using a sheet shaped heat generating body, and more particularly to a thin heat generating bag having high heat generating performance and inside which the heat generating composition is not displaced.

2. Disclosure of the Related Art

Conventionally, heat generating bags wherein an air-permeable bag containing a heat generating composition with oxidizable metals such as iron powder as the prinicipal component, and emit heat upon contact with oxygen in the air, have been widely used as pocket heaters. In Utility Model Laid-Open (Kokai) Publication No. SHO 59-071618, an air-permeable heat generating bag in the shape of a horseshoe or a trapezoid which is used as a heat generating bag etc. for shoes or slippers is disclosed.

All of these heat generating bag for footwear are air-permeable bags containing moist powder which is a mixture of iron powder, activated carbon, a water holding agent, an inorganic electrolyte etc. These heat generating bag for footwear are sealed in a non-air permeable bag and kept there until they are used. Upon use, the outer bag is torn, and the heat generating bag for footwear is taken out for application and use inside a footwear.

However, conventional heat generating bag for footwear were inconvenient in that, upon use inside a pair of shoes, the bag would be warm and comfortable only when the wearer stayed still, but the temperature of the heat generating bag for footwear would suddenly rise and become too hot when the wearer walked. In contrast, when the heat generating temperature of the bag was set at a substantially low temperature to secure a comfortable temperature upon walking, insufficient heat was obtained when staying still.

Moreover, conventional heat generating bag for footwear were inconvenient in that, upon application inside a pair of shoes, they would be twisted or their heat generating composition powder would be displaced to one side during use and cause an uncomfortable feeling to the wearer. Furthermore, if a heat generating bag was used with such heat generating composition remaining at one side, limited portions where the heat generating composition concentrated occasionally showed high temperatures.

Under these circumstances, there has been a demand for a development of a heat generating bag for footwear which provides a comfortable temperature regardless of the state of use, which is thin, avoids uncomfortableness of the wearer, and is easily manufactured.

SUMMARY OF THE INVENTION

After careful examination for solving the above-mentioned problems, the inventors of the present invention et al. found that these problems may be solved by having a mixture of hot-melt adhesive powder and heat generating composition powder held in the pores of vegetable fiber non-woven fabrics, and packing inside an air-permeable bag a sheet shaped heat generating body obtained through heat compression on a mold compressor. The present invention was thus reached.

In other words, the present invention provides a heat generating bag for footwear which is made by having multiporous vegetable fiber non-woven fabrics superposed in a plurality of layers, at least one of such layers holding the heat generating composition powder and the hot-melt adhesive powder, such one layer and at least a portion of other layers in contact therewith being adhered to each other by heat compression on a mold compressor, and the obtained sheet shaped being impregnated with water or an inorganic electrolyte and being packed in an air-permeable bag.

Moreover, the present invention provides a manufacturing method of a heat generating bag for footwear comprising a vegetable fiber non-woven fabric (a), a vegetable fiber non-woven fabric (b) which is placed at the bottom face of the vegetable fiber non-woven fabric (a), and a vegetable fiber non-woven fabric (c) which is placed on the top face of the vegetable fiber non-woven fabric (a), and having the heat generating composition powder and the hot-melt adhesive powder held in the pores of the vegetable fiber non-woven fabric (a) and between the layers of the vegetable fiber non-woven fabrics (a) and (c), the vegetable fiber non-woven fabric (a) and at least a portion of other non-woven fabrics in contact therewith being adhered to each other by implementing heat compression on a mold compressor, and the sheet-shaped heat generating body which is impregnated with water or an inorganic electrolyte being held in an air-permeable bag.

Furthermore, the present invention has found that the above-referred problems may be solved if the mixture of heat generating composition powder is held in the pores of at least one layer of the non-woven fabric layers being built up by the adhesion of water, and the above-mentioned layers are compressed on a mold compressor and the obtained sheet shaped heat generating body is packed in an air-permeable bag.

In other words, the present invention provides a heat generating bag for footwear which is made by having a plurality of layers of vegetable fiber non-woven fabrics being superposed, the heat generating composition powder being held in at least one layer among such plurality of layers, the superposed layers having the heat generating composition powder being formed into a sheet-like shape by the compressive force of a mold compressor and the adhesion of water, and the obtained sheet shaped product being impregnated with water or an inorganic electrolyte thereby forming a sheet-shaped heat generating body, and such heat generating body being thereafter packed in an air-permeable bag.

Moreover, the present invention provides a manufacturing method of a heat generating bag used in footwear, wherein a vegetable fiber non-woven fabric (b) is placed at the bottom face of a vegetable fiber non-woven fabric (a) by adhesion of water, and the heat generating composition powder is sprinkled onto the top face of the vegetable fiber non-woven fabric (a) so that it will be held in the pores, and after superposing a vegetable fiber non-woven fabric (c) on the vegetable fiber non-woven fabric (a) and compressing the fabrics on the mold compressor, a sheet shaped heat generating body which is impregnated with water or an inorganic electrolyte is packed inside an air-permeable bag.

The above-described heat generating composition powder may have iron powder and activated carbon, or iron powder, activated carbon and an inorganic electrolyte as its principal component.

The above-mentioned hot-melt adhesive powder has a softening point of 40–200° C., and is to be added in an amount of 0.1 to 20 parts by weight per iron powder 100 parts by weight.

DETAILED DESCRIPTION OF THE PREFERRED EMBODIMENTS

Figure 1:
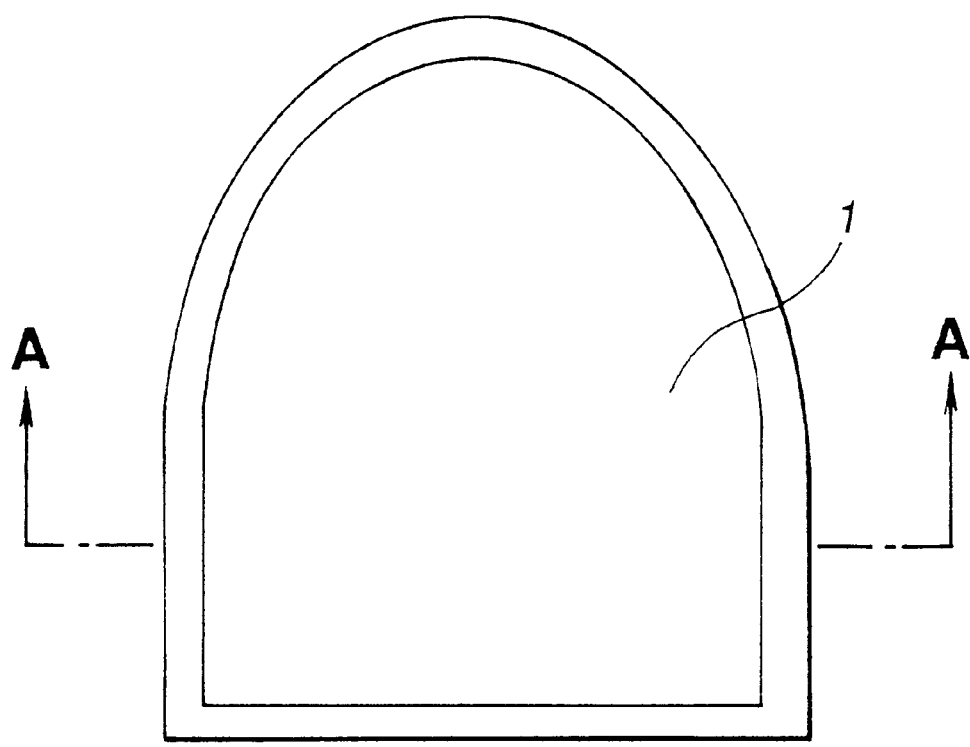
FIG. 1 is a plane view of the heat generating bag for footwear according to embodiment 1.

The heat generating bag for footwear according to the embodiments of the present invention are applied mainly inside footwear such as shoes and slippers so as to keep the feet warm.

Embodiment 1

In the heat generating bag according to embodiment 1, the heat generating composition and the hot-melt adhesive powder are held in the pores of the layered multiporous vegetable fiber non-woven fabrics and between such layers, and a sheet-shaped heat generating body is obtained by having the above-mentioned layered non-woven fabrics built up by adhesion of the hot-melt adhesive powder via heat compression, and the obtained sheet-shaped heat generating body is packed inside an air-permeable bag.

The manufacturing method of heat generating bag for footwear according to embodiment 1 is as follows: Namely, a vegetable fiber non-woven fabric (b) is placed at the bottom face of a multiporous vegetable fiber non-woven fabric (a), and the heat generating composition powder and the hot-melt adhesive powder are sprinkled onto the top face of the vegetable fiber non-woven fabric (a) so as to be held in the pores, and a vegetable fiber non-woven fabric (c) is placed on the top face of the vegetable fiber non-woven fabric (a). The layered non-woven fabrics obtained above are compressed on a mold compressor, made into a sheet-like shape, and then impregnated with water or an inorganic electrolyte, thereby forming a sheet shaped heat generating body, and the obtained sheet shaped heat generating body is packed inside an air-permeable bag.

In the heat generating bag for footwear according to embodiment 1, the heat generating composition and the hot-melt adhesive powder are held in the layered non-woven fabrics. The heat generating composition may be held in the non-woven fabrics by ways of, for example, (1) dispersing a mixture of powder materials such as iron powder, activated carbon, inorganic electrolyte and water, etc. on the non-woven fabrics, and thereafter adding vibration or pressing the non-woven fabrics, so that the powder materials are held in the non-woven fabrics, or (2) sprinkling a mixture of powder materials such as iron powder, activated carbon, inorganic electrolyte, etc. on the non-woven fabrics and adding vibration to the obtained non-woven fabrics, so that the powder materials are held in the pores, and thereafter sprinkling water on the non-woven fabrics, or (3) spreading a mixture of powder materials other than iron powder, activated carbon or an inorganic electrolyte and adding vibration, so that the powder materials are held in the pores, and thereafter dispersing the inorganic electrolyte on the non-woven fabrics and having the non-woven fabrics impregnated with such solution. Among the methods above, methods (2) and (3) are preferable because the heat generating composition is more easily held in the pores of the non-woven fabrics when the fabrics do not include moisture, and (3) is even more preferable because by using methods (1) and (2), it is difficult to have the inorganic electrolyte permeated into the entire portion of the non-woven fabric in a homogeneous manner, and moreover, the oxidizable metal powder will start to oxidize when it is mixed with water, etc. For the reasons above, method (3) is normally used to hold the heat generating composition in the non-woven fabrics.

Next, the manufacturing method mainly using method (3) is explained in regard to the heat generating bag for footwear according to embodiment 1.

The vegetable fiber non-woven fabric (a) in embodiment 1 should be capable of holding a mixture of heat generating composition materials which emit heat upon contact with air and which are used in the forms of powder (hereinafter referred to as the "heat generating composition powder"), and it should also have a high moisture retention ability. The main component of the vegetable fiber non-woven fabric (a) can be, for example, vegetable fibers such as pulp, cotton, hemp, rayon or acetate (in the present invention, regenerated fibers such as rayon and acetate are included in the vegetable fibers). The non-woven fabric may be produced by the entangling of the fibers, or by using binders such as synthetic resin or adhesive agents at such degree that would not provide a heat-adhesive property to the non-woven fabric. Although the thickness varies depending on the amount of the heat generating composition powder it holds, the normal thickness is 0.5–10 mm, preferably 1–7 mm. The basis weight is usually 20–150 g/m$^2$, preferably 30–100 g/m$^2$.

The vegetable fiber non-woven fabric (b) is for preventing leakage of the heat generating composition powder from the bottom face of the vegetable fiber non-woven fabric (a), and is used by being placed at the bottom face of the vegetable fiber non-woven fabric (a). Non-woven fabrics having vegetable fibers such as pulp, cotton, hemp, rayon or acetate, or paper-type materials such as tissue papers as the principal components are the desirable materials of the vegetable fiber non-woven fabric (b). The vegetable fiber non-woven fabric (b) normally has a denser construction than the vegetable fiber non-woven fabric (a), and the normal basis weight is 10–70 g/m$^2$, preferably 15–40 g/m$^2$.

The vegetable fiber non-woven fabric (c) is for holding the heat generating composition powder remaining on the top face of the vegetable fiber non-woven fabric (a) not being fully held in the vegetable fiber non-woven fabric (a), and for preventing the leakage of the heat generating composition powder onto the top face of the vegetable fiber non-woven fabric (a). The vegetable fiber non-woven fabric (c) is used by being superposed on top of the vegetable fiber non-woven fabric (a). Desirable materials of the vegetable fiber non-woven fabric (c) are those having many pores and high moisture retention ability, for example, non-woven fabric formed by vegetable fibers such as pulp, cotton, hemp, rayon or acetate.

Although the thickness of the vegetable fiber non-woven fabric (c) varies depending on the amount of the heat generating composition powder it holds, it is usually 0.2–7 mm, preferably 0.5–5 mm. The basis weight is usually 10–100 g/m$^2$, preferably 20–80 g/m$^2$.

Oxidizable metal powder, activated carbon etc. are the raw materials composing the heat generating composition powder. Inorganic electrolyte is one of the components of the heat generating composition powder if it is mixed with the above-mentioned raw materials in a solid state, but will not be included in the heat generating composition powder if it is to be used as an inorganic electrolyte in the impregnation after the formation of the sheet.

Although iron powder, aluminum powder, etc. are included in the oxidizable metal powder, normally used is iron powder, namely, reduced iron powder, atomized iron powder, electrolyte iron powder, etc.

Activated carbon is used not only as a reaction auxiliary agent, but also as a water holding agent, and coconut husk carbon, wood flour carbon, peat carbon etc. are normally used.

As an inorganic electrolyte, preferably used are chloride of alkaline metals, alkaline earth metals, heavy metals non-woven fabrics chloride, or alkaline metal sulfate, for example, sodium potassium chloride, calcium chloride, magnesium chloride, ferric chloride, sodium sulfate etc.

The heat generating composition is a mixture of the above-mentioned heat generating composition powder and water or an inorganic electrolyte. A high polymer water holding agent, hydrogen restrainer, consolidation inhibitor etc. may also be added upon desire.

The particle size of the heat generating composition powder is usually 60 meshes or less, preferably at least 50% of the heat generating composition powder being 100 meshes or less.

The blending rate of the heat generating composition powder as a whole varies depending on the nature of the non-woven fabric and the aimed heating performance, and may not be uniformly specified. One example of the blending rate is, activated carbon in an amount of 5 to 20 parts by weight, inorganic electrolyte in an amount of 1.5 to 10 parts by weight, and water in an amount of 25 to 60 parts by weight per iron powder 100 parts by weight.

The hot-melt adhesive agent according to the present invention is fused by heat and pressure, and is selected taking into consideration its mixing property with the heat generating composition, softening point of the hot-melt adhesive agent, particle size, adhering method, adhering property to the non-woven fabric, etc. The preferable softening point is 40–200° C. Ethylene/vinyl acetate copolymer, ionomer etc., thermoplastic homopolymers such as polyethelene, polypropylene, polystyrene etc., or blends of these polymers, or hot-melt adhesive agents having these thermoplastic resins as a base polymer and mixing adhesive auxiliary agents, wax etc. are used as the hot-melt adhesive agent. These adhesive powder agents can be used alone or combined.

Concerning the particle size of the hot-melt adhesive powder, he diameter is normally 0.02–2 mm, preferably, 0.05–1.5 mm, and ore preferably 0.1–0.8 mm.

The adding amount of the hot-melt adhesive powder varies depending on the adding method, and may not be uniformly specified. However, the adding amount of the hot-melt adhesive powder would be normally 0.1 to 20 parts by weight, preferably 0.3 to 12 parts by weight, and more preferably 0.5 to 7 parts by weight per iron powder 100 parts by weight.

Next, an example of the structure and the manufacturing method of the heat generating bag for footwear is explained referring to the drawings. However, the present invention is not limited to such example.

Figure 2:
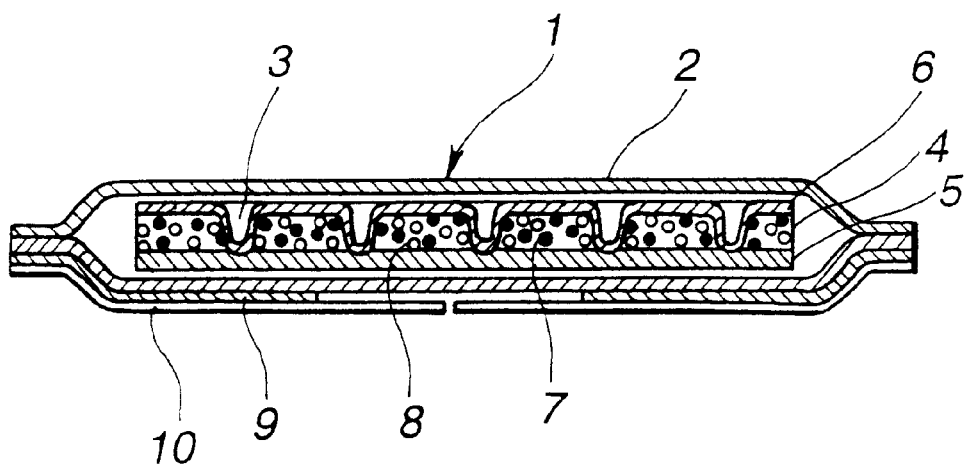
FIG. 2 is a cross-sectional view taken along line A—A in FIG. 1.

FIG. 1 is a plane view of a heat generating bag 1 for footwear. FIG. 2 is a cross-sectional view taken along line A—A of the heat generating bag 1 for footwear. Reference numeral 2 shows an air-permeable bag. Reference numeral 3 shows a sheet shaped heat generating body. Reference numeral 4 shows a vegetable fiber non-woven fabric (a). Reference numeral 5 shows a vegetable fiber non-woven fabric (b). Reference numeral 6 shows a vegetable fiber non-woven fabric (c). Reference numeral 7 shows a heat generating composition. Reference numeral 8 shows hot-melt adhesive powder. Reference numeral 9 shows an adhesive agent. Reference numeral 10 shows a separating paper.

Figure 3:
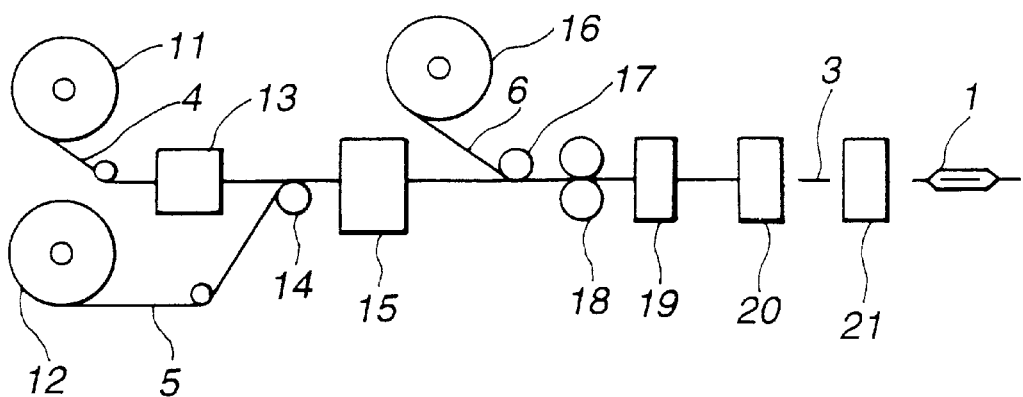
FIG. 3 is a process of manufacturing a heat generating bag for footwear according to embodiment 1.

FIG. 3 is an example of the manufacturing process of the resent invention. Reference numeral 11 shows a roll of the vegetable fiber non-woven fabric (a). Reference numeral 12 shows a roll of the vegetable fiber non-woven fabric (b). Reference numeral 13 shows a water sprinkling portion. Reference numeral 14 shows a roller portion. Reference numeral 15 shows a sprinkling portion of the heat generating composition powder and the hot-melt adhesive powder. Reference numeral 16 shows a roll of the vegetable fiber non-woven fabric (c). Reference numeral 17 shows a roller portion. Reference numeral 18 shows a heat compressing portion. Reference numeral 19 shows a cutting portion. Reference numeral 20 shows a sprinkling portion of water or electrolyte. Reference numeral 21 shows an air-permeable bag packing portion.

Water is sprinkled to the bottom face of the vegetable fiber non-woven fabric (a)4 at the water sprinkling portion 13, and the vegetable fiber non-woven fabric (b)5 is placed at the bottom face of the vegetable fiber non-woven fabric (a) 4 at the roller portion 14 by the adhesion of water. Subsequently, the heat generating composition powder and the hot-melt adhesive powder are sprinkled at the heat generating composition powder sprinkling portion 15, and vibration is added thereafter so that the powder is held in the pores of the vegetable fiber non-woven fabric (a). The vegetable fiber non-woven fabric (c)6 is superposed at the roller portion 17, heat-compressed at the heat-compressing portion 18, and cut into a desired size at the cutting portion 19. Subsequently, water or electrolyte is sprinkled at the water or electrolyte sprinkling portion 20, and a sheet shaped heat generating body 3 is thus produced. Finally, by packing the sheet shaped heat generating body 3 in an air-permeable bag at the packing portion 21, a heat generating bag 1 for footwear is obtained.

In embodiment 1, other than a method of sprinkling the heat generating composition powder on the vegetable fiber non-woven fabric (a) and then sprinkling the hot-melt adhesive powder thereon, the following methods may be used: a method of mixing the hot-melt adhesive powder with the heat generating composition powder and sprinkling such mixture on the top face of the vegetable fiber non-woven fabric (a); a method of sprinkling the hot-melt adhesive powder and thereafter sprinkling the heat generating composition powder; or a method of sprinkling the heat generating composition powder before or after the sprinkling of the hot-melt adhesive powder, etc. However, by using the method of sprinkling the hot-melt adhesive powder before the sprinkling of the heat generating composition powder, there is a chance that the above-stated hot-melt adhesive powder may fill up the pores of the vegetable fiber non-woven fabric (a) or pass through the vegetable fiber non-woven fabric (a) depending on the particle size of the hot-melt adhesive powder. Therefore, it is desirable to use either the method of sprinkling the mixture of the hot-melt adhesive powder and the heat generating composition powder on the top face of the vegetable fiber non-woven fabric (a), or the method of sprinkling the hot-melt adhesive powder after the sprinkling of the heat generating composition powder. If the hot-melt adhesive powder is to be sprinkled apart from the heat generating composition powder, the adhesive powder agent can be sprinkled homogeneously on the entire surface of the non-woven fabric (a), or otherwise can be partially sprinkled in a dot-like or a lattice-like manner.

Although the amount of the heat generating composition held in the non-woven fabric is determined depending on the thickness of the non-woven fabric, or the aimed thickness or the desired heat generating performance of the heat generating body, the normal rate is 300–5000 g/m$^2$ of the vegetable fiber non-woven fabric (a), and preferably 700–2000 g/m$^2$. If the amount held is less than 300 g, there will be a lower temperature and a shorter duration upon emission of heat. If the amount held exceeds 5000 g, the heat generating body will be thicker and the formation of a thin and soft sheet will be difficult.

Heat compression may be implemented by passing the layers of non-woven fabric through a heat presser or a heating roller. Although heat compression may be implemented on a flat surface or a flat roller, it is preferable that at least one side of the compression surface has an embossed surface so that the mold fixation effect will be enhanced while maintaining the softness of the sheet-like product. Although there is no specific limitation to the shape of the embossed surface, it should have such shape to allow the heat generating composition powder to move to the non-compressed portion upon heat compression, and therefore, the embossed surface is normally formed to have the shapes of waves, turtlebacks, rings, polka dots, nets etc.

Although there is no specific limitation to the rate of the protruding area to the embossed surface, the normal rate is 0.5–60.0%, preferably 5.0–40.0%.

The temperature upon heat compression and the terms of compression vary depending on the materials of the vegetable fiber non-woven fabrics (a), (b) and (c), the softening point of the hot-melt adhesive agent and the amount of the heat generating composition powder being held. For example, upon heat compression conducted by a heating roller, the temperature is approximately 70–300° C., with a linear load of 0.1–250 kg/cm. With the non-woven fabrics layers being in a compressed condition by the roller, and the hot-melt adhesive powder lying on the surface contacting the protrusion is fused and the shape is secured, and then a sheet-like product is formed.

As for the thickness of the sheet-shaped heat generating body, it is preferable that the heat generating body is made as thin as possible, within a range capable of holding an amount of the heat generating composition required for certain heat generating performances such as desired temperatures or duration upon emission of heat. Such thickness is normally 2.5 mm or less.

Concerning the size and the shape of the sheet shaped heat generating body, there is no specific limitation as long as it comprises a size and a shape that fits into an air-permeable bag. The sheet shaped heat generating body is normally formed in the shapes of toes of soles, rectangles, squares, circles, semicircles, ellipses, semi-ellipses etc.

The amount of water or the inorganic electrolyte to be impregnated is equal to the total amount of water or the inorganic electrolyte determined by the composition rate of the heat generating composition. Water or the solution is provided and impregnated by spraying, dripping or roller attachment, and a sheet shaped heat generating body is thus obtained.

In the present invention, an air-permeable bag is a bag with at least one surface being composed of air-permeable packaging material. Pores of the packaging material need not be homogeneously provided on the entire surface, but can be partially provided.

Although there is no specific limitation in the material of the air-permeable packaging material, it should be capable of providing an amount of air required for the emission of heat of the heat generating composition powder and should have a strength to endure the friction or the rubbing pressure upon use. Examples of possible packaging materials are non-woven fabric attached to composite resin film such as polyethylene, polypropylene, polyester, polyvinylidene chloride comprising fine pores for air-permeability, or independently-used multiporous film, or non-woven fabric attached to multiporous film, etc.

Generally, the quantity of permeability of an air-permeable heat generating bag used in footwear is larger than that of a heat generating bag used on human bodies, because the circulation of the air and the heat retention inside the footwear are poor.

There is no limitation to the shape of the air-permeable bag if it has a size and shape to fit inside the footwear, and can be formed in the shapes of rectangles, squares, circles, semicircles, semi-ellipses or shapes of soles. However, it is particularly desirable to form the bag in the shapes of the toes of soles, semicircles, ellipses, semi-ellipses etc., so that it will match the application portion inside the footwear.

In embodiment 1, an adhesive agent layer can be provided in whole or in part on one side of the heat generating bag so that the fixation at the application portion is enhanced.

Concerning the adhesive agent used as the adhesive agent layer, any agent may be used if such agent has sufficient adhesion to prevent the displacement of the bag when it is attached inside the footwear and has a non-sticking property to the inside of the footwear when being removed. For example, a non-sticking organic solvent adhesive agent made of rubber, acrylic resin, vinyl acetate copolymer, etc., or a water-type adhesive agent are preferably used.

If an adhesive agent layer is to be provided, such layer will be covered with a separating paper before use, so that the layer will not stick to other things. Papers having the same nature as the generally-sold adhering sheets, tapes and stickers can be used as separating paper, and such papers are coated with a release agent made of silicon etc. so as to facilitate removal of the paper from the surface of the adhesive agent layer.

In order to prevent the oxidization of oxidizable metal, the heat generating bag for footwear according to embodiment 1 is sealed inside a non-air-permeable outer bag and kept there until it is used.

FIGS. 2 and 3 indicate a heat generating bag for footwear having a heat generating body of three superposed layers of non-woven fabrics and an example for manufacturing such heat generating body. However, the heat generating bag according to the present invention may have a two layer construction of vegetable fiber non-woven fabrics (a) and (b), a combination of two layers and three layers, or multi-layers.

Thus, by holding the heat generating composition and the hot-melt adhesive powder in the vegetable fiber non-woven fabrics with many pores, and forming the heat generating body into a sheet-like shape via heat compression and packing the same in an air-permeable bag, obtained was a heat generating bag for footwear which provides a comfortable temperature either when both walking and staying still, and comprises a heat generating composition which is not displaced to one side, and yet is soft and avoids an uncomfortable feeling of the wearer.

Embodiment 1 is specifically explained below by example 1, but the present invention is not limited to such example.

EXAMPLE 1

A wooden pulp non-woven fabric with a thickness of about 1.1 mim and a basis weight of 40 g/m² and having a bottom face moistened by sprinkling water was superposed on a tissue paper with a basis weight of 25 g/m². Subsequently, a mixture of 90 parts of iron powder, 8 parts of activated carbon, 2 parts of a high polymer water holding agent and 1 part of ethylene vinyl acetate copolymer resin powder was sprayed on the above-mentioned wooden pulp non-woven fabric at a rate of 1500 g/m², and vibration was added so that the mixed agent would be held in the pores of the non-woven fabric.

By superposing a wooden pulp non-woven fabric with a thickness of 1.2 mm and a basis weight of 60 g/m² on the top face of the above-described non-woven fabric, and then passing such fabrics through a roller-type heat compressor having a dot-like embossed face provided on the upper roller surface and being set at 200° C. and a linear load of 133 kg/cm, a sheet shaped product was obtained. This sheet shaped product was cut into the shape of a toe of a shoe sole approximately 60 mm×80 mm in size, on which salt water was sprinkled with a density of 20% at the rate of 570 g/m² Thus, a sheet shaped heat generating body having a thickness of 2 mm was obtained.

A nylon non-woven fabric having a basis weight of 50 g/m² and polyethylene film having a thickness of 50 μ were attached to form the sheet, and the non-woven fabric side of the sheet was coated with an acrylic ester adhesive agent. The surface coated with the adhesive agent above was covered with a separating paper, and a non-air-permeable sheet was obtained.

A polyethylene micro multiporous membrane having a Gurley permeability of 100 cc/20 sec as set forth in ASTM D762 was placed on the non-air-permeable sheet so that the polyethylene sides come into contact with one another, and the sheet was cut into the shape of a toe of a shoe sole approximately 80 mm×100 mm in size and was heat-sealed in the vicinity of the curve of the toes, thereby producing an air-permeable bag.

After packing the above-described sheet shaped heat generating body in the bag above, the opening was heat sealed, and a heat generating bag for footwear approximately 2.3 mm in thickness was obtained. Meanwhile, the non-woven fabric did not come off, nor did the heat generating composition powder fall out.

Figure 4:
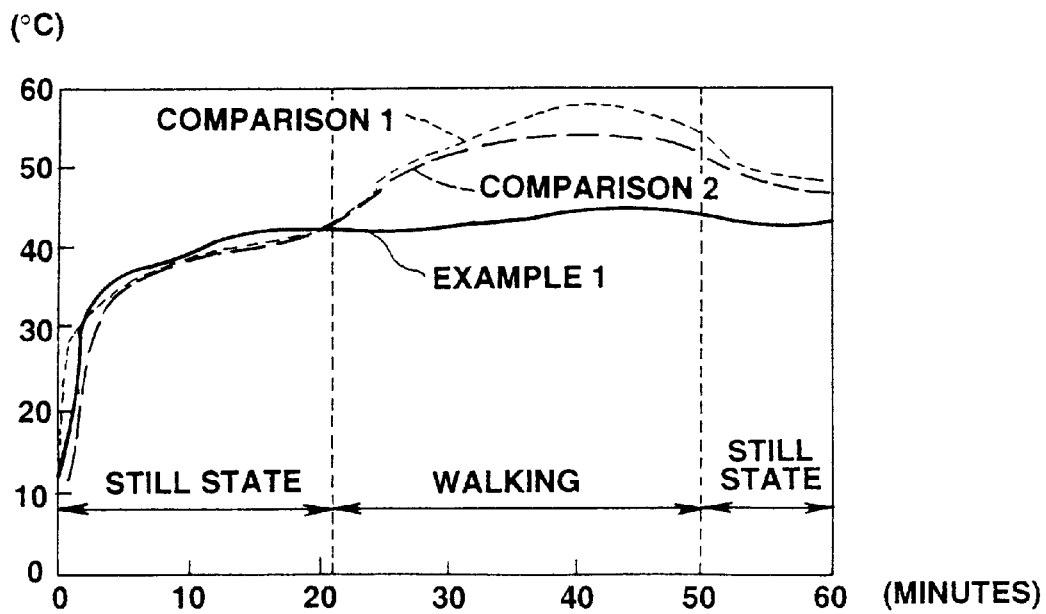
FIG. 4 is a chart showing the heat generating performance of the heat generating bag for footwear according to embodiment 1 and comparisons 1 and 2.

The heat generating bag for footwear was sealed inside a non-air-permeable outer bag and was kept there for 2 days, and was taken out of the outer bag and attached to the bottom portion of the toes of a pair of sports shoes with the micro multiporous membrane side facing upward, and the heat generating performance of the heat generating bag for footwear was measured as follows:

A copper-constantan thermocouple was attached to the center portion of the top face of the heat generating bag for footwear, and the wearer sat down on a chair for 20 minutes under a temperature of 10° C. and a humidity of 60%, and then walked for 30 minutes at a speed of 5 km/hr, and then sat down on a chair again for 10 minutes. Measurements were made regarding the change in the temperature of the heat generating bag for footwear when staying still and walking, and the results are shown in FIG. 4.

Consequently, the heat generating bag reached a temperature of 30° C. after being applied for 2 minutes, and maintained a constant temperature of approximately 40° C. when the wearer stayed still and was comfortably used. Furthermore, there was no sudden rise in the temperature when the wearer walked, and the temperature remained within the approximate range of 40° C. to 45° C. and was comfortably used.

Upon application, the heat generating composition of the heat generating bag for footwear was not displaced to one side, and was easily applied. Moreover, the heat generating composition was not displaced to one side when the wearer walked and the wearer did not feel any uncomfortableness.

Comparison 1

A heat generating bag for footwear having a thickness of approximately 2 mm was manufactured by inserting a heat generating composition which is a mixture of 5 g of iron powder, 0.5 g of activated carbon, 0.5 g of salt, 1.5 g of water and 0.2 g of a high polymer water holding agent into a bag having the same permeability of the air as in embodiment 1.

The heat generating bag for footwear was sealed inside a non-air-permeable outer bag and kept there for 2 days, and was taken out of the outer bag and was attached to the bottom portion of the toes of the same sports shoes as in example 1 with the side of the micro porous membrane facing upward, and the heat generating performance of the heat generating bag for footwear was measured in the same way as in example 1. The results are indicated in FIG. 4.

As a consequence, the heat generating bag reached a temperature of 30° C. after being applied for 2 minutes, and was comfortably used when the wearer stayed still. However, when the wearer walked, the temperature rose to a high of 59° C. When the wearer stayed still after walking, the temperature remained to be as high as 50° C.

In addition, the heat generating composition of the heat generating bag for footwear obtained from comparison 1 was displaced to one side when being applied, and when the wearer walked, it caused uncomfortableness to the wearer. Furthermore, the heat generating composition was solidified after use.

Comparison 2

A heat generating bag for footwear having a thickness of approximately 2 mm was produced in the same manner as in comparison 1.

The heat generating bag for footwear was sealed inside a non-air-permeable outer bag and was kept there for 2 days, and was taken out of the outer bag and attached to the bottom portion of the toes of safety shoes with the side of the microporous membrane facing upward, and the heat generating performance of the heat generating bag for footwear was measured in the same way as in example 1. The results are indicated in FIG. 4.

As a consequence, the heat generating bag reached a temperature of 30° C. after being applied for 2 minutes, and was comfortably used when the wearer stayed still. However, when the wearer walked, the temperature rose to a high of 53° C. When the wearer stayed still after walking, the temperature remained to be as high as 50° C.

Embodiment 2

Embodiment 2 according to the present invention is explained below. In embodiment 2, contents which are the same with embodiment 1 will be referred to with the same reference numerals, or will be mentioned "the same", so that any redundant explanation may be omitted.

In a heat generating bag for footwear according to embodiment 2, the heat generating composition is held in the superposed layers of the non-woven fabric. The heat generating bag for footwear has the same plane shape as in the heat generating bag 1 for footwear which is shown in FIG. 1.

Figure 5:
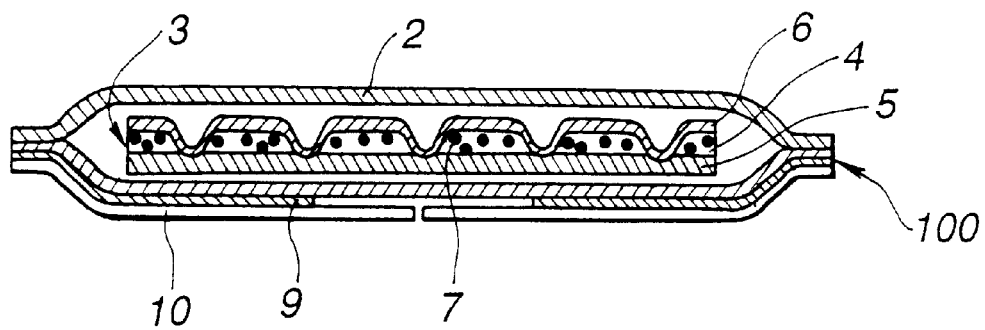
FIG. 5 is a cross-sectional view of the heat generating bag for footwear according to embodiment 2, which corresponds to FIG. 2.
Figure 6:
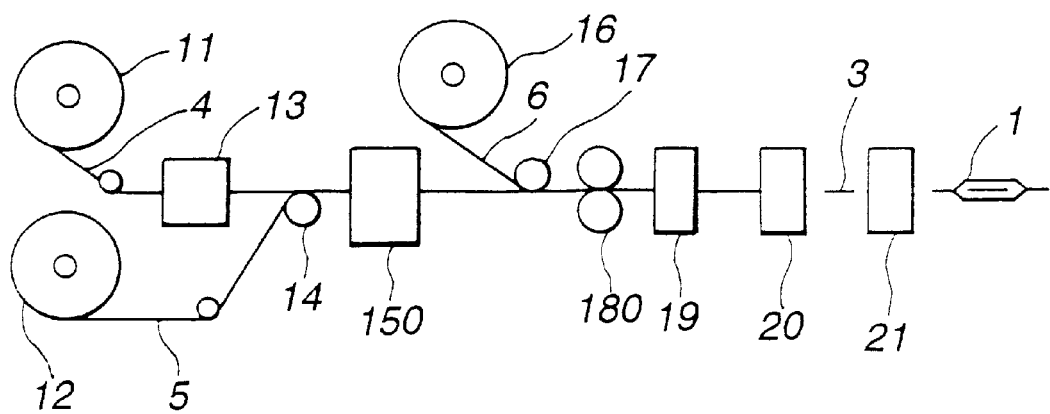
FIG. 6 is a manufacturing process of the heat generating bag for footwear according to embodiment 2.

FIG. 5 is a cross-sectional view of a portion of the heat generating bag for footwear 100 corresponding to the portion shown in FIG. 2. FIG. 6 is an example of the manufacturing process.

In FIG. 6, reference numeral 150 is a sprinkling portion of the heat generating composition powder, and reference numeral 180 is a compressing portion by a mold compressor.

In the heat generating bag for footwear 100 according to embodiment 2, water is sprinkled on the bottom face of the vegetable fiber non-woven fabric (a)4 at the water sprinkling portion 13, and the vegetable fiber non-woven fabric (b)5 is placed at the bottom face of the vegetable fiber non-woven fabric (a)4 by the adhesion of water at the roller portion 14. Subsequently, the heat generating composition powder is sprinkled at the heat generating composition powder sprinkling portion 150 and vibration is added, so that the powder is held in the pores of the vegetable fiber non-woven fabric (a). At the rolling portion 17, the vegetable fiber non-woven fabric (c)6 is superposed on the vegetable fiber non-woven fabric (a) obtained above and then heat-compressed at the heat-compressing portion 180, and cut into a desired size at the cutting portion 19. Subsequently, water or an electrolyte is sprinkled at the water or electrolyte sprinkling portion 20, and a sheet shaped heat generating body 3 is produced. Finally, by packing the sheet shaped heat generating body 3 into an air-permeable bag at the packing portion 21, a heat generating bag for footwear 100 is obtained.

In the present invention, by adhering water between the layers of the non-woven fabrics, the fabrics are closely attached to each other by the adhesion of water.

In regard to the method of adhering water, the amount of water adhered should be adjustable and water should be homogeneously adhered. For example, a method of spraying water, or a method of adhering water by a roller may be used.

If water is adhered to the bottom face of the vegetable fiber non-woven fabric (a), the amount of water should be able to prevent leakage of the heat generating composition powder from the bottom face of the vegetable fiber non-woven fabric (a). Although the adhering amount varies according to the basis weight and the material of the non-woven fabric, it is usually 10–200 g/m$^2$, preferably, 20–120 g/m$^2$. Instead of using a method of adhering water to the bottom face of the vegetable fiber non-woven fabric (a), it is possible to use a method of adhering water on the top face of the vegetable fiber non-woven fabric (b). Otherwise, water may be applied to the bottom face of the vegetable fiber non-woven fabric (c) when the vegetable fiber non-woven fabric (c) is superposed. In these cases, water may be adhered in the same manner as in adhering water to the bottom face of the vegetable fiber non-woven fabric (a).

The amount of the heat generating composition held in the non-woven fabric is determined according to the thickness of the non-woven fabric, or the aimed thickness or the desired heat generating performance of the heat generating body. However, the normal rate is 300–5000 g/m$^2$ of the vegetable fiber non-woven fabric (a), and preferably 700–2000 g/m$^2$. If the amount held is less than 300 g/m$^2$, there will be a lower temperature and a shorter duration upon emission of heat. However, if the amount held is over 5000 g/m$^2$, the heat generating body will be thicker and formation of a thin and soft sheet will be difficult.

Compression may be implemented by passing the layers of on-woven fabric through a pressing device or a roller. Although compression may be implemented on a flat surface or a flat roller, it is preferable that at least one side of the compression surface has an embossed surface so that there is higher effect of mold fixation while maintaining the softness of the sheet shaped product. Although there is no specific limitation to the shape of the embossment, it should have such shape to allow the heat generating composition powder to move to the non-compressed portion upon compression, and therefore, the embossed surface is normally formed in the shapes of waves, turtlebacks, rings, polka dots, nets etc.

Although the rate of the protruding area to the embossed surface is not specifically limited, the normal rate is 0.5–60.0%, preferably, 5.0–40.0%.

Although compression may be conducted at room temperature, a desirable temperature condition for heating is 70–300° C. Water is adhered while the non-woven fabrics are being layered, and therefore, by adding heat, the surface on which water is adhered and the surface contacting such surface may be molded and fixed to each other in a more secured manner via the moistening and heating effect. The linear load of compression varies depending upon the material of the vegetable fiber non-woven fabrics (a), (b) and (c), and the heat generating composition powder being held by such fabric. The normal linear load is 0.1–250 kg/cm.

The thickness, the size, the shape of the sheet shaped heat generating body, the definition of the air-permeable bag, and the amount of water or the inorganic electrolyte to be impregnated are the same as in embodiment 1. In order to enhance attachment of the heat generating bag for footwear at the portion of application, an adhesive agent layer as in embodiment 1 may be provided on one side of the heat generating bag in part or in whole in the same manner as in embodiment 1.

For the purpose of preventing the oxidization of the oxidizable metal, the heat generating bag for footwear according to embodiment 2 is sealed inside a non-air-permeable outer bag and kept there until it is used.

Although FIGS. 5 and 6 show a heat generating bag for footwear having a sheet shaped heat generating body built up in three layers and an example of the manufacturing thereof, the heat generating bag according to the present invention may have a two layer construction of vegetable fiber non-woven fabrics (a) and (b), a combination of two layers and three layers, or multilayers.

Thus, by keeping the heat generating composition powder in the multiporous vegetable fiber non-woven fabric, and forming the heat generating body into a sheet-like shape via heat compression and adhesion of water and packing into an air-permeable bag, a heat generating bag for footwear was obtained. Such heat generating bag for footwear provides a comfortable temperature regardless of walking or staying still, and prevents the heat generating composition from being displaced to one side and yet is soft and does not bring uncomfortableness to the wearer.

Embodiment 2 is specifically explained below by example 2, but the present invention is not limited to such example.

EXAMPLE 2

A wooden pulp non-woven fabric with a thickness of 1.1 mm and a basis weight of 40 g/m$^2$ and having a bottom face moistened by sprinkling water was superposed on a tissue paper with a basis weight of 25 g/m². Then, a mixture of 90 parts of iron powder, 8 parts of activated carbon, and 2 parts of a high polymer water holding agent was sprinkled on the above-mentioned wooden pulp non-woven fabric at a rate of 1500 g/m², and vibration was added so that the mixed agent would be held in the pores of the non-woven fabric.

Next, a wooden pulp non-woven fabric having a thickness of 1.2 mm and a basis weight of 60 g/m² was superposed on the top face of the non-woven fabric above in the same manner as in embodiment 1. A heat generating bag for footwear having a thickness of approximately 2.3 mm was thus manufactured. During the manufacture, the heat generating composition powder did not fall out.

Subsequently, the heat generating bag for footwear was sealed inside a non-air-permeable outer bag and was kept there for 2 days, and was taken out of the outer bag and attached to the bottom portion of the toes of sports shoes with the micro multiporous membrane side facing upward. The heat generating performance of the heat generating bag for footwear was measured in the same way as in example 1. Consequently, a favorable result was obtained as in example 1.

As explained above, the heat generating bag according to the present invention has a uniform thickness and is not powder is held in the non-woven fabric. Furthermore, since non-woven fabrics having high water holding property are used, the heat generating bag is made less thick and softer. Therefore, no uncomfortableness is felt while it is used. Moreover, since the non-woven fabric being used has a high water holding property, emission of heat is effectively conducted for a long period of time.

Moreover, a constant temperature is obtained regardless of the state of use, when walking or staying still.

In addition, the sheet shaped product is not detached during the manufacturing process, and may be transferred and transported without fail. Furthermore, a footwear heat generating body with a homogeneously distributed heat generating composition is obtained.

What is claimed is:

1. A heat generating body for footwear comprising:
   a sheet shaped heat generating body, and
   an air-permeable bag containing said sheet shaped heat generating body,
   wherein said sheet shaped heat generating body includes vegetable fiber non-woven fabrics having many pores and which are superposed in a plurality of layers, and a heat generating composition powder having a particle size of 60 mesh or smaller and hot-melt adhesive powder held in the pores of at least one layer of the superposed non-woven fabric layers wherein said one layer includes top and bottom surfaces,
   said one non-woven fabric layer being adhered on said top and bottom surfaces to other of said non-woven fabrics by a bond formed by fused particles of said hot-melt powder and being impregnated with water or an inorganic electrolyte.

2. A heat generating bag for footwear comprising:
   a sheet shaped heat generating body, and
   an air-permeable bag containing said sheet shaped heat generating body,
   wherein said sheet shaped heat generating body includes:
   a vegetable fiber non-woven fabric (a);
   a vegetable fiber non-woven fabric (b) placed at the bottom face of said vegetable fiber non-woven fabric (a);
   a vegetable fiber non-woven fabric (c) placed on the top face of said vegetable fiber non-woven fabric (a), and
   a heat generating composition powder and hot-melt adhesive powder being held in pores of said vegetable fiber non-woven fabric (a) and between the layers of said vegetable fiber non-woven fabric (a) and said non-woven fabric (c), wherein said hot-melt adhesive powder constitutes 0.1 to 20 parts by weight per 100 parts per weight of said iron powder,
   and said vegetable fiber non-woven fabric (a) and at least a portion of other non-woven fabrics contacting said non-woven fabric (a) being adhered to each other by a bond formed by fused particles of said hot-melt powder and being impregnated with water or an inorganic electrolyte.

3. A heat generating bag for footwear according to claim 1 or 2, wherein said hot-melt adhesive powder has a softening point of 40–200° C. and is to be added in an amount of 0.1 to 20 parts by weight per iron powder 100 parts by weight.

4. A heat generating bag for footwear comprising:
   a sheet shaped heat generating body in an air-permeable bag containing said sheet shaped heat generating body,
   wherein said sheet shaped heat generating body includes:
   vegetable fiber non-woven fabrics with many pores which are superposed in a plurality of layers, and
   a heat generating composition powder having a particle size of 60 mesh or smaller held in at least one layer of said superposed non-woven fabric layers, said one layer having top and bottom surfaces,
   said top and bottom surfaces of said one layer being adhered to different ones of said non-woven fabrics into a sheet shape by a bond formed by the adhesion of water when said fabrics are compressed, and being impregnated with water or an inorganic electrolyte.

5. A heat generating bag for footwear comprising:
   a sheet shaped heat generating body and an air-permeable bag containing said sheet shaped heat generating body,
   wherein said sheet shaped heat generating body includes:
   a vegetable fiber non-woven fabric (a);
   a vegetable fiber non-woven fabric (b) placed at the bottom face of said vegetable fiber non-woven fabric (a);
   a vegetable fiber non-woven fabric (c) placed on the top face of said vegetable fiber non-woven fabric (a), and
   a heat generating composition powder having a particle size of 60 mesh or smaller being held in pores of said vegetable fiber non-woven fabric (a) and between the layers of said vegetable fiber non-woven fabric (a) and said vegetable fiber non-woven fabric (c),
   said fabrics of said sheet shaped heat generating body being adhered into a sheet-like shape by a bond formed by the adhesion of water when said fabrics are compressed and being impregnated with water or an inorganic electrolyte.

6. A heat generating bag for footwear according to any one of claims 1, 2, 4, or 5, wherein said heat generating composition powder has iron powder and activated carbon, or iron powder, activated carbon and an inorganic electrolyte as its main component.

* * * * *